(12) United States Patent
Srinivasan et al.

(10) Patent No.: US 10,596,219 B2
(45) Date of Patent: Mar. 24, 2020

(54) LOGIC-DRIVEN LAYOUT VERIFICATION

(75) Inventors: Sridhar Srinivasan, Tualatin, OR (US);
Fedor G. Pikus, Beaverton, OR (US);
Patrick D. Gibson, Tualatin, OR (US);
Padmaja Susarla, McLean, VA (US)

(73) Assignee: Mentor Graphics Corporation, Wilsonville, OR (US)

(*) Notice: Subject to any disclaimer, the term of this patent is extended or adjusted under 35 U.S.C. 154(b) by 0 days.

(21) Appl. No.: 13/017,788

(22) Filed: Jan. 31, 2011

(65) Prior Publication Data

US 2011/0320990 A1 Dec. 29, 2011

Related U.S. Application Data

(63) Continuation of application No. 12/952,196, filed on Nov. 22, 2010, now abandoned.

(60) Provisional application No. 61/348,209, filed on May 25, 2010.

(51) Int. Cl.
*G06F 17/50* (2006.01)
*A61K 38/00* (2006.01)
*A61K 39/395* (2006.01)
*A61K 47/02* (2006.01)
*A61K 38/48* (2006.01)

(52) U.S. Cl.
CPC .......... *A61K 38/00* (2013.01); *A61K 38/4846* (2013.01); *A61K 39/395* (2013.01); *A61K 47/02* (2013.01)

(58) Field of Classification Search
CPC ............. G06F 17/5081; G06F 17/5068; G06F 17/5077; G06F 17/505; G06F 17/5031; G06F 2217/12; G06F 2217/84; G06F 17/5022; G06F 2217/06; G06F 17/5036; G06F 17/5045; G06F 17/5072; G06F 2217/02; G06F 17/5009; G06F 2217/74; G06F 2217/04; G06F 2217/08; G06F 2217/38; G06F 2217/40; G06F 2217/64; G06F 15/7867; G06F 17/50; G06F 17/5018; G06F 17/5054; G06F 17/5063; G06F 1/266; G06F 2217/62; G06F 2217/78; G06F 2217/80; G06F 7/588; G06F 7/76; G01R 31/2848; G01R 31/31724; H01L 21/027; H01L 28/88; G03F 1/36
USPC .................................................. 716/110–114
See application file for complete search history.

(56) References Cited

U.S. PATENT DOCUMENTS 6,944,839 B2 *  9/2005  Chevallier et al. ........... 716/112
2001/0052107 A1 * 12/2001  Anderson .......... G06F 17/5081
                                                   716/52
2002/0100005 A1 *  7/2002  Anderson .......... G06F 17/5081
                                                   716/52

(Continued)

*Primary Examiner* — Binh C Tat (57) ABSTRACT

A check for determining the appropriateness of physical design data is provided, where the check includes both a physical component and a logical component. Based upon the logical component of the check, portions of the physical design data that correspond to the logical component are identified and selected. After the portions of the physical design data corresponding to the logical component have been selected, this physical design data can be provided to a physical design analysis tool, along with the physical component of the design check. The physical design analysis tool can then use the physical component of the design check to perform an analysis of the selected physical design data.

14 Claims, 7 Drawing Sheets

(56) References Cited

U.S. PATENT DOCUMENTS

| | | | |
|---|---|---|---|
| 2002/0166103 A1* | 11/2002 | Rittman et al. ................. | 716/11 |
| 2003/0229866 A1* | 12/2003 | Allen et al. ........................ | 716/5 |
| 2005/0251771 A1* | 11/2005 | Robles ................ | G06F 17/5022 |
| | | | 716/52 |
| 2006/0265675 A1* | 11/2006 | Wang ................... | G06F 17/5081 |
| | | | 716/52 |
| 2007/0174797 A1* | 7/2007 | Luo ................... | G05B 19/41875 |
| | | | 716/56 |
| 2009/0106715 A1* | 4/2009 | Pikus ................... | G06F 17/5081 |
| | | | 716/106 |
| 2010/0058260 A1* | 3/2010 | Correale, Jr. ....... | G06F 17/5068 |
| | | | 716/106 |
| 2010/0115487 A1* | 5/2010 | Tripathi .............. | G06F 17/5077 |
| | | | 716/122 |

* cited by examiner

LOGIC-DRIVEN LAYOUT VERIFICATION

RELATED APPLICATIONS

This application claims priority to U.S. Provisional Patent Application No. 61/348,209, entitled "Logic-Driven Layout Verification," filed on May 25, 2010, and naming Patrick D. Gibson, et al. as inventors, which application is incorporated entirely herein by reference.

This application is a continuation-in-part of U.S. patent application Ser. No. 12/952,196, entitled "Logic-Driven Layout Verification," filed on Nov. 22, 2010, and naming Patrick D. Gibson, et al. as inventors, which application is incorporated entirely herein by reference.

FIELD OF THE INVENTION

The present invention is directed to an integrated verification platform for performing verification of an integrated circuit design using electronic design automation operations. Various implementations of the invention may be useful for performing physical verification of a circuit design based upon logical design information.

BACKGROUND OF THE INVENTION

Many microdevices, such as integrated circuits, have become so complex that these devices cannot be manually designed. For example, even a simple microprocessor may have millions and millions of transistors that cooperate to form the components of the microprocessor. As a result, electronic design automation tools have been created to assist circuit designers in analyzing a circuit design before it is manufactured. These electronic design automation tools typically will execute one or more electronic design automation (EDA) processes to verify that the circuit design complies with specified requirements, identify problems in the design, modify the circuit design to improve its manufacturability, or some combination thereof. For example, some electronic design automation tools may provide one or more processes for simulating the operation of a circuit manufactured from a circuit design to verify that the design will provides the desired functionality. Still other electronic design automation tools may alternately or additionally provide one or more processes for confirming that a circuit design matches the intended circuit schematic, for identifying portions of a circuit design that do not comply with preferred design conventions, for identifying flaws or other weaknesses the design, or for modifying the circuit design to address any of these issues. Examples of electronic design automation tools include the Calibre® family of software tools available from Mentor Graphics Corporation of Wilsonville, Oreg.

As electronic devices continue to have smaller and smaller features and become more complex, greater sophistication is being demanded from electronic design automation tools. For example, manufacturing technology faces increasing challenges related to yield, reliability, and leakage and timing variability. These challenges have led to a host of design for manufacturability (DFM) techniques because process improvements alone are not sufficient. The early DFM applications addressed yield issues caused by random defects and catastrophic failures. These process-based, or physical, DFM solutions identify and correct design areas that are vulnerable to functional failures, such as shorts and opens. Wire spreading, via doubling, and critical area analysis have become mainstream.

At 65 nm and below, parametric failures become the dominant yield-limiting mechanism. Manufacturing variations affecting power, timing, or other performance specifications cause parametric yield loss. These failure mechanisms are addressed by the next generation of DFM solutions, Electrical DFM (EDFM). EDFM tools address device or interconnect parameters that are affected by process variability and can adversely impact chip performance. Lithography and chemical-mechanical polishing (CMP) modeling, combined with device characterization and timing analysis, capture the effects of process variations on chip performance. Some advanced EDFM methodologies can optimize designs, on a gate-by-gate basis if desired, to reduce variability and improve timing. Electrically-driven optical proximity correction (OPC) tools tweak the manufacturing process itself to implement the optimized solution proposed by an EDFM tool.

A fundamental principle behind all EDFM solutions is that these tools are aware of design characteristics and requirements, such as power and timing, and can use them to estimate the effect of a particular manufacturing process on the design, or to influence the manufacturing process. To do this, EDFM tools should have the ability to analyze logical netlist and physical layout in context.

Most EDFM tools are still limited by the restrictions inherent in a traditional verification flow, which is very compartmentalized. The flow typically includes 1) design rule checking (DRC), layout analysis, and parameter extraction; 2) layout vs. schematic (LVS) and logical analysis (electrical rule checking, or ERC); 3) layout parasitic extraction (LPE); and 4) simulation. At the same time, the design schematic goes through a separate tool chain, only meeting the layout data during the LVS step.

The DRC and physical DFM tools have the most detailed layout information, but almost no understanding of the logical circuit to be implemented by a physical layout. The LVS tool, on the other hand, performs very complex logical analysis, and can be aware of the design intent, but it has only limited information about the physical layout. It is desirable to have an integrated verification platform and corresponding methods for cross-domain design-dependent DFM, or logic-driven verification.

BRIEF SUMMARY OF THE INVENTION

Various aspects of the invention related to performing a physical analysis of a circuit design based upon logical information. According to some implementations of the invention, a check for determining the appropriateness of physical design data is provided, where the check includes both a physical component and a logical component. For example, the check may specify that transistors to which the check is applicable have a minimum width. Further, the check may specify that the minimum width requirement is only applicable to transistors used in a 1-bit static random access memory (SRAM) circuit. With some implementations of the invention, the circuit design check may be in the form of a rule, such as the design rules employed in design rule decks by the Calibre® family of circuit design verification tools available from Mentor Graphics Corporation of Wilsonville, Oreg., and by other electronic design automation design verification tools known to those of ordinary skill in the art. With other implementations of the invention, the circuit design check may be additionally or alternatively embedded in the design data, e.g. in the schematic netlist design file.

Based upon the logical component of the check, various implementations of the invention will automatically identify portions of the physical design data that correspond to the logical component (that is, in the provided example, 1-bit SRAM circuits). With some implementations, the corresponding physical design data may be selected and obtained directly from a design database. With still other implementations of the invention, the logical components specified in the check may be cross referenced in a logical design database, to determine a correlation between, for example, arbitrary logical structure names employed in the check and corresponding logical objects obtained by extracting logical information from the physical design data.

After the portions of the physical design data corresponding to the logical component have been selected, this physical design data can be provided to a physical design analysis tool, along with the physical component of the design check. The physical design analysis tool can then use the physical component of the design check to perform an analysis of the selected physical design data. The analysis of the selected physical design data includes various layout analyses and verifications. With some implementations of the invention, the results of the analysis can be reported to a user as visual images, new design data, or both. Alternately or additionally, various implementations may then modify the selected physical design data based upon the results of the analysis. These and other aspects of the invention will be discussed in more detail below.

DETAILED DESCRIPTION OF THE INVENTION

Overview

Figure 1:
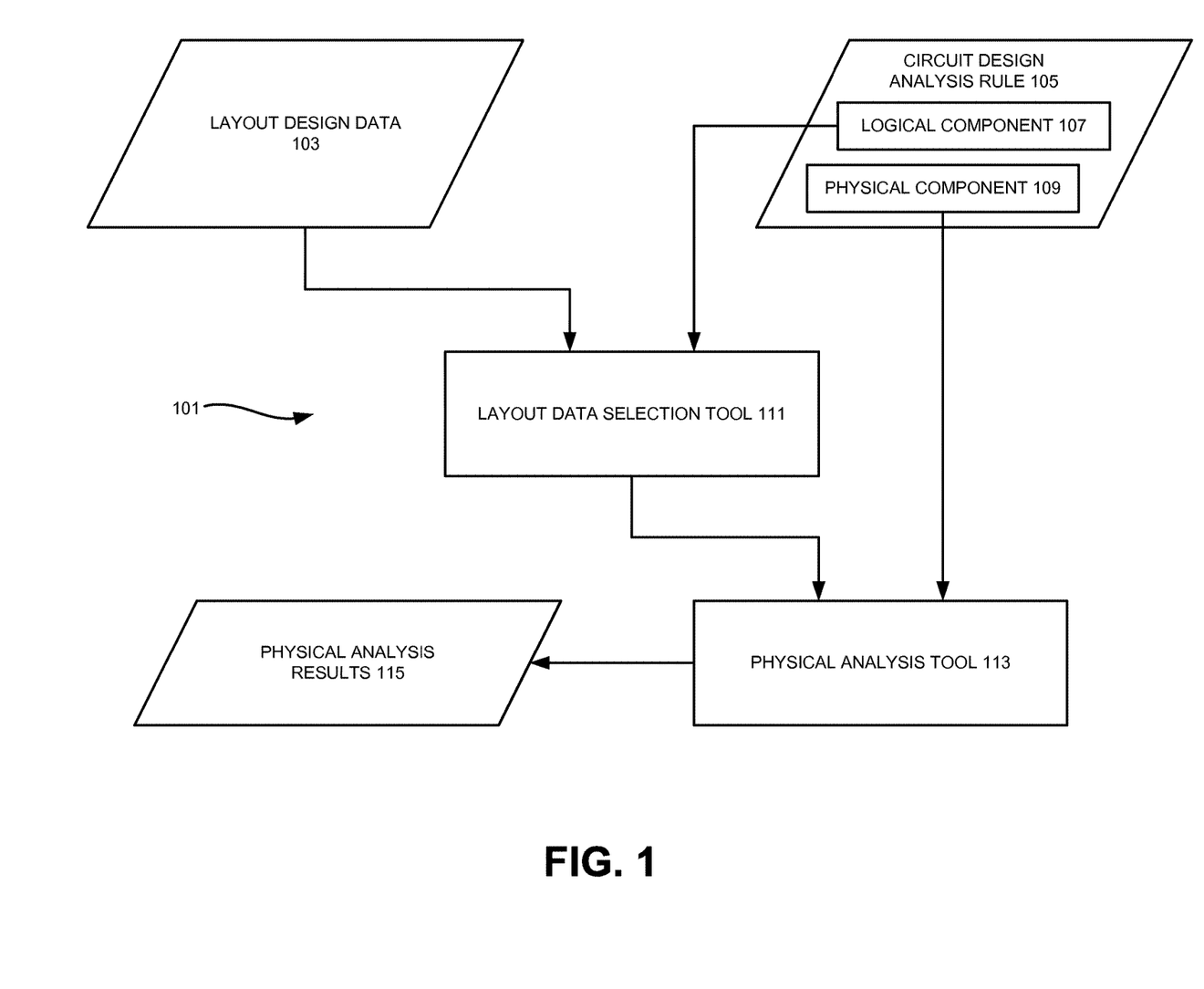
FIG. 1 illustrates a process flow that might be implemented according to various embodiments of the invention.

FIG. 1 illustrates an example of a flow process 101 that may be employed according to various implementations of the invention. As seen in this figure, layout design data 103 is analyzed in the flow process 101. As used herein, the terms "design" and "design data" encompass data describing an entire microdevice, such as an integrated circuit device or micro-electromechanical system (MEMS) device. These terms also are intended, however, to encompass a smaller set of data describing one or more components of an entire microdevice, such as a layer of an integrated circuit device, or even a portion of a layer of an integrated circuit device. Still further, the terms "design" and "design data" also are intended to encompass data describing more than one microdevice, such as data to be used to create a mask or reticle for simultaneously forming multiple microdevices on a single wafer. Also, unless otherwise specified, the term "design" as used herein is intended to encompass any type of design, including both physical layout designs and logical designs.

In the flow process 101, a user (for example, an integrated circuit designer or manufacturer) provides criteria for checking the appropriateness of a design. Typically, these checking criteria will be in the form of a circuit design analysis rule 105. Additionally or alternatively, these checking criteria may be embedded in the logical design data. As seen in FIG. 1, the circuit design analysis rule 105 includes a logical component 107 and a physical component 109. The logical component 107 will specify some type of structure or other object in a logical circuit design, such as a netlist. Typically, the logical component 107 will be a circuit device (for example, MOS field-effect transistors) or an arrangement of circuit devices into a particular configuration (for example, a 1-bit SRAM circuit), but various implementations of the invention may allow the logical component 107 to specify any desired logical design object.

The physical component 109 similarly may be any criteria that can be applied to analyze physical design data. Typically, the physical component 109 will be some type of physical measurement criteria, such as a minimum width determination, a maximum distance determination, an area ratio determination, and the like. Of course, the physical component 109 may include any desired criteria desired for analyzing physical circuit design data.

According to various implementations of the invention, the logical component 107 is extracted from the circuit design analysis rule 105. A layout data selection tool 111 then selects physical design data from among the layout design data 103 that corresponds to the logical component 107. With some implementations of the invention, the layout selection tool 111 may select the corresponding physical design data directly from the layout design data 103. In some situations, however, the logical component 107 may use arbitrary information, such as circuit structure names or circuit device names, that do not have any context for the layout design data 103. With these implementations, the layout selection tool 111 may incorporate or otherwise employ the services of a translation unit (not show). The translation unit can translate the arbitrary logical component information, such as a circuit structure or device names from a schematic netlist, with corresponding logical component information extracted from the layout design data 103. Using the information provided by the translation unit, the layout selection tool 111 can then select the desired physical design data from the layout design data 103, and provide it to a physical analysis tool 113. The physical analysis tool 113 can then use the physical component 109 from the circuit design analysis rule 105 to analyze the selected physical design data, thereby producing physical analysis results 115. The physical analysis results 115 may be processed by the translation unit for naming some elements with layout and schematic names.

Operating Environment

The execution of various electronic design automation processes according to embodiments of the invention may be implemented using computer-executable software instructions executed by one or more programmable computing devices, by computer-executable software instructions tangibly and non-transitorily stored on a computer readable medium (such as a magnetic or optical memory storage device) for execution by one or more programmable computing devices, or some combination thereof. Accordingly, the components and operation of a generic programmable computer system on which various embodiments of the invention may be employed will first be described. Further, because of the complexity of some electronic design automation processes and the large size of many circuit designs, various electronic design automation tools are configured to operate on a computing system capable of simultaneously running multiple processing threads. The components and operation of a computer network having a host or master computer and one or more remote or servant computers therefore will be described with reference to FIG. 2. This operating environment is only one example of a suitable operating environment, however, and is not intended to suggest any limitation as to the scope of use or functionality of the invention.

Figure 2:
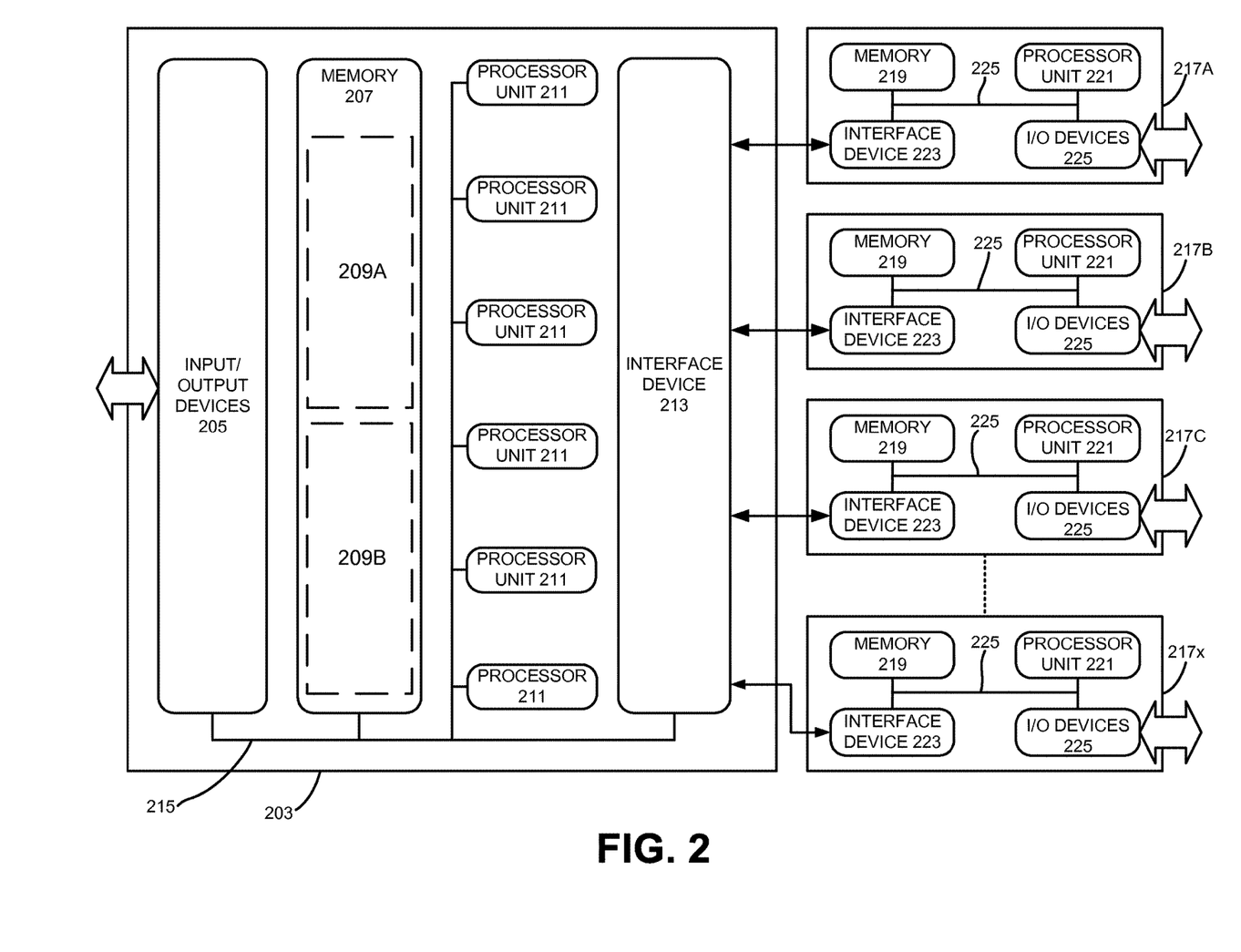
FIG. 2 illustrates an example of a computing system that may be used to implement various embodiments of the invention.

In FIG. 2, the computer network 201 includes a master computer 203. In the illustrated example, the master computer 203 is a multi-processor computer that includes a plurality of input and output devices 205 and a memory 207. The input and output devices 205 may include any device for receiving input data from or providing output data to a user. The input devices may include, for example, a keyboard, microphone, scanner or pointing device for receiving input from a user. The output devices may then include a display monitor, speaker, printer or tactile feedback device. These devices and their connections are well known in the art, and thus will not be discussed at length here.

The memory 207 may similarly be implemented using any combination of computer readable media that can be accessed by the master computer 203. The computer readable media may include, for example, microcircuit memory devices such as read-write memory (RAM), read-only memory (ROM), electronically erasable and programmable read-only memory (EEPROM) or flash memory microcircuit devices, CD-ROM disks, digital video disks (DVD), or other optical storage devices. The computer readable media may also include magnetic cassettes, magnetic tapes, magnetic disks or other magnetic storage devices, punched media, holographic storage devices, or any other medium that can be used to store desired information.

As will be discussed in detail below, the master computer 203 runs a software application for performing one or more operations according to various examples of the invention. Accordingly, the memory 207 stores software instructions 209A that, when executed, will implement a software application for performing one or more operations. The memory 207 also stores data 209B to be used with the software application. In the illustrated embodiment, the data 209B contains process data that the software application uses to perform the operations, at least some of which may be parallel.

The master computer 203 also includes a plurality of processor units 211 and an interface device 213. The processor units 211 may be any type of processor device that can be programmed to execute the software instructions 209A, but will conventionally be a microprocessor device. For example, one or more of the processor units 211 may be a commercially generic programmable microprocessor, such as Intel® Pentium® or Xeon™ microprocessors, Advanced Micro Devices Athlon™ microprocessors or Motorola 68K/Coldfire® microprocessors. Alternately or additionally, one or more of the processor units 211 may be a custom-manufactured processor, such as a microprocessor designed to optimally perform specific types of mathematical operations. The interface device 213, the processor units 211, the memory 207 and the input/output devices 205 are connected together by a bus 215.

Figure 3:
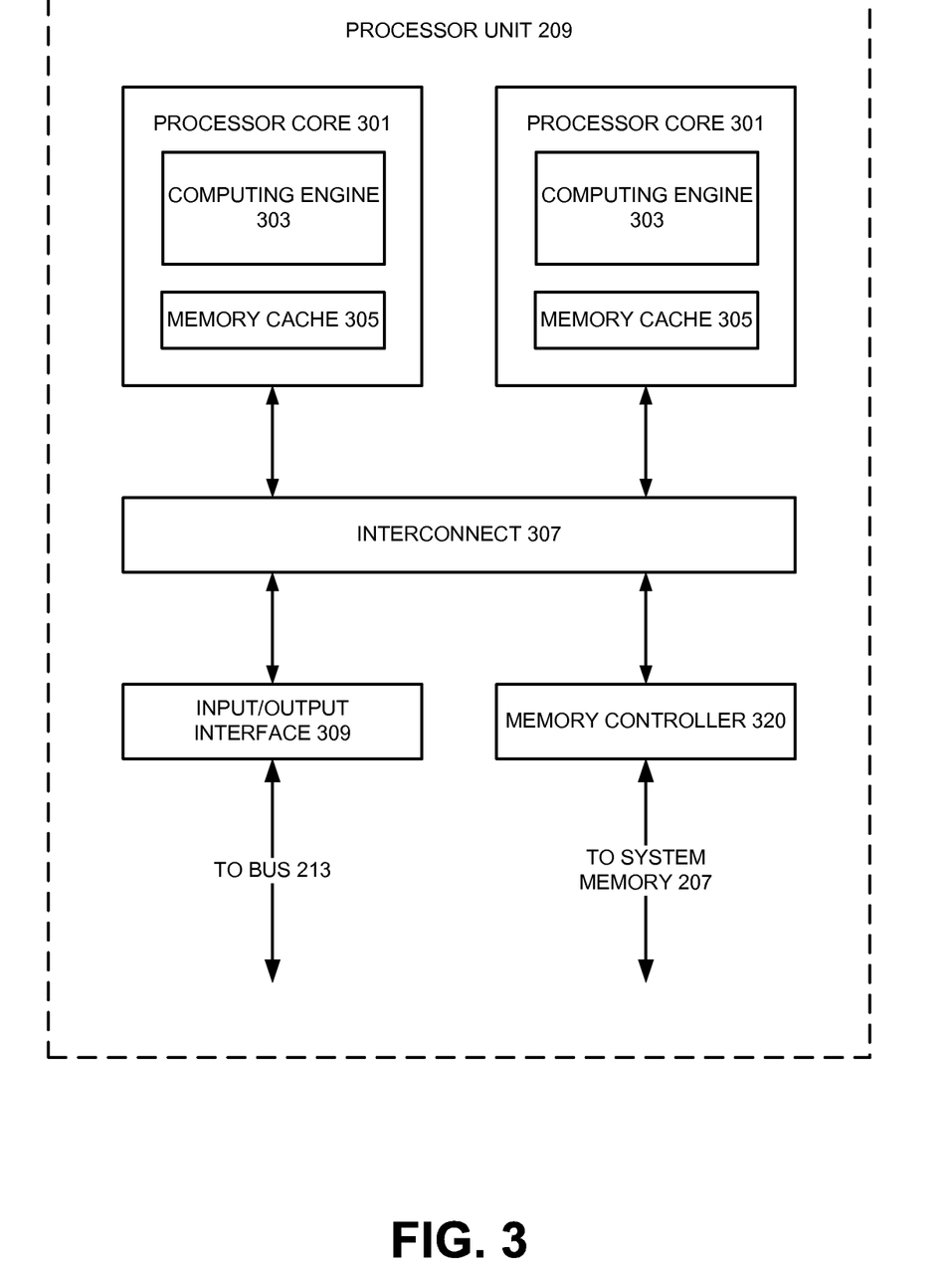
FIG. 3 illustrates an example of a multi-core processor unit that may be in a programmable computer, such as the programmable computer illustrated in FIG. 2, to implement various embodiments of the invention.

With some implementations of the invention, the master computing device 203 may employ one or more processing units 211 having more than one processor core. Accordingly, FIG. 3 illustrates an example of a multi-core processor unit 211 that may be employed with various embodiments of the invention. As seen in this figure, the processor unit 211 includes a plurality of processor cores 301. Each processor core 301 includes a computing engine 303 and a memory cache 305. As known to those of ordinary skill in the art, a computing engine contains logic devices for performing various computing functions, such as fetching software instructions and then performing the actions specified in the fetched instructions. These actions may include, for example, adding, subtracting, multiplying, and comparing numbers, performing logical operations such as AND, OR, NOR and XOR, and retrieving data. Each computing engine 303 may then use its corresponding memory cache 305 to quickly store and retrieve data and/or instructions for execution.

Each processor core 301 is connected to an interconnect 307. The particular construction of the interconnect 307 may vary depending upon the architecture of the processor unit 301. With some processor cores 301, such as the Cell microprocessor created by Sony Corporation, Toshiba Corporation and IBM Corporation, the interconnect 307 may be implemented as an interconnect bus. With other processor units 301, however, such as the Opteron™ and Athlon™ dual-core processors available from Advanced Micro Devices of Sunnyvale, Calif., the interconnect 307 may be implemented as a system request interface device. In any case, the processor cores 301 communicate through the interconnect 307 with an input/output interface 309 and a memory controller 311. The input/output interface 309 provides a communication interface between the processor unit 301 and the bus 215. Similarly, the memory controller 311 controls the exchange of information between the processor unit 301 and the system memory 207. With some implementations of the invention, the processor units 301 may include additional components, such as a high-level cache memory accessible shared by the processor cores 301.

While FIG. 3 shows one illustration of a processor unit 301 that may be employed by some embodiments of the invention, it should be appreciated that this illustration is representative only, and is not intended to be limiting. For example, some embodiments of the invention may employ a master computer 203 with one or more Cell processors. The Cell processor employs multiple input/output interfaces 309 and multiple memory controllers 311. Also, the Cell processor has nine different processor cores 301 of different types. More particularly, it has six or more synergistic processor elements (SPEs) and a power processor element (PPE). Each synergistic processor element has a vector-type computing engine 303 with 428×428 bit registers, four single-precision floating point computational units, four integer computational units, and a 556 KB local store memory that stores both instructions and data. The power processor element then controls that tasks performed by the synergistic processor elements. Because of its configuration, the Cell processor can perform some mathematical operations, such as the calculation of fast Fourier transforms (FFTs), at substantially higher speeds than many conventional processors.

It also should be appreciated that, with some implementations, a multi-core processor unit 211 can be used in lieu of multiple, separate processor units 211. For example, rather than employing six separate processor units 211, an alternate implementation of the invention may employ a single processor unit 211 having six cores, two multi-core processor units each having three cores, a multi-core processor unit 211 with four cores together with two separate single-core processor units 211, etc.

Returning now to FIG. 2, the interface device 213 allows the master computer 203 to communicate with the servant computers 217A, 217B, 217C . . . 117x through a communication interface. The communication interface may be any suitable type of interface including, for example, a conventional wired network connection or an optically transmissive wired network connection. The communication interface may also be a wireless connection, such as a wireless optical connection, a radio frequency connection, an infrared connection, or even an acoustic connection. The interface device 213 translates data and control signals from the master computer 203 and each of the servant computers 217 into network messages according to one or more communication protocols, such as the transmission control protocol (TCP), the user datagram protocol (UDP), and the Internet protocol (IP). These and other conventional communication protocols are well known in the art, and thus will not be discussed here in more detail.

Each servant computer 217 may include a memory 219, a processor unit 221, an interface device 223, and, optionally, one more input/output devices 225 connected together by a system bus 227. As with the master computer 203, the optional input/output devices 225 for the servant computers 217 may include any conventional input or output devices, such as keyboards, pointing devices, microphones, display monitors, speakers, and printers. Similarly, the processor units 221 may be any type of conventional or custom-manufactured programmable processor device. For example, one or more of the processor units 221 may be commercially generic programmable microprocessors, such as Intel® Pentium® or Xeon™ microprocessors, Advanced Micro Devices Athlon™ microprocessors or Motorola 68K/Coldfire® microprocessors. Alternately, one or more of the processor units 221 may be custom-manufactured processors, such as microprocessors designed to optimally perform specific types of mathematical operations. Still further, one or more of the processor units 221 may have more than one core, as described with reference to FIG. 3 above. For example, with some implementations of the invention, one or more of the processor units 221 may be a Cell processor. The memory 219 then may be implemented using any combination of the computer readable media discussed above. Like the interface device 213, the interface devices 223 allow the servant computers 217 to communicate with the master computer 203 over the communication interface.

In the illustrated example, the master computer 203 is a multi-processor unit computer with multiple processor units 211, while each servant computer 217 has a single processor unit 221. It should be noted, however, that alternate implementations of the invention may employ a master computer having single processor unit 211. Further, one or more of the servant computers 217 may have multiple processor units 221, depending upon their intended use, as previously discussed. Also, while only a single interface device 213 or 223 is illustrated for both the master computer 203 and the servant computers, it should be noted that, with alternate embodiments of the invention, either the computer 203, one or more of the servant computers 217, or some combination of both may use two or more different interface devices 213 or 223 for communicating over multiple communication interfaces.

With various examples of the invention, the master computer 203 may be connected to one or more external data storage devices. These external data storage devices may be implemented using any combination of computer readable media that can be accessed by the master computer 203. The computer readable media may include, for example, microcircuit memory devices such as read-write memory (RAM), read-only memory (ROM), electronically erasable and programmable read-only memory (EEPROM) or flash memory microcircuit devices, CD-ROM disks, digital video disks (DVD), or other optical storage devices. The computer readable media may also include magnetic cassettes, magnetic tapes, magnetic disks or other magnetic storage devices, punched media, holographic storage devices, or any other medium that can be used to store desired information. According to some implementations of the invention, one or more of the servant computers 217 may alternately or additionally be connected to one or more external data storage devices. Typically, these external data storage devices will include data storage devices that also are connected to the master computer 203, but they also may be different from any data storage devices accessible by the master computer 203.

It also should be appreciated that the description of the computer network illustrated in FIG. 2 and FIG. 3 is provided as an example only, and it not intended to suggest any limitation as to the scope of use or functionality of alternate embodiments of the invention.

Electronic Design Automation

As previously noted, various embodiments of the invention are related to electronic design automation. In particular, various implementations of the invention may be used to improve the operation of electronic design automation software tools that identify, verify and/or modify design data for manufacturing a microdevice, such as a microcircuit. As used herein, the terms "design" and "design data" are intended to encompass data describing an entire microdevice, such as an integrated circuit device or micro-electro-mechanical system (MEMS) device. This term also is intended to encompass a smaller set of data describing one or more components of an entire microdevice, however, such as a layer of an integrated circuit device, or even a portion of a layer of an integrated circuit device. Still further, the terms "design" and "design data" also are intended to encompass data describing more than one microdevice, such as data to be used to create a mask or reticle for simultaneously forming multiple microdevices on a single wafer. It should be noted that, unless otherwise specified, the term "design" as used herein is intended to encompass any type of design, including both a physical layout design and a logical design.

Designing and fabricating microcircuit devices involve many steps during a 'design flow' process. These steps are highly dependent on the type of microcircuit, its complexity, the design team, and the fabricator or foundry that will manufacture the microcircuit from the design. Several steps are common to most design flows, however. First, a design specification is modeled logically, typically in a hardware design language (HDL). Once a logical design has been created, various logical analysis processes are performed on the design to verify its correctness. More particularly, software and hardware "tools" verify that the logical design will provide the desired functionality at various stages of the design flow by running software simulators and/or hardware emulators, and errors are corrected. For example, a designer may employ one or more functional logic verification processes to verify that, given a specified input, the devices in a logical design will perform in the desired manner and provide the appropriate output.

In addition to verifying that the devices in a logic design will provide the desired functionality, some designers may employ a design logic verification process to verify that the logical design meets specified design requirements. For example, a designer may create rules such as, e.g., every transistor gate in the design must have an electrical path to ground that passes through no more than three other devices, or every transistor that connects to a specified power supply also must be connected to a corresponding ground node, and not to any other ground node. A design logic verification process then will determine if a logical design complies with specified rules, and identify occurrences where it does not.

After the logical design is deemed satisfactory, it is converted into physical design data by synthesis software. This physical design data or "layout" design data may represent, for example, the geometric elements that will be written onto a mask used to fabricate the desired microcircuit device in a photolithographic process at a foundry. For conventional mask or reticle writing tools, the geometric elements typically will be polygons of various shapes. Thus, the layout design data usually includes polygon data describing the features of polygons in the design. It is very important that the physical design information accurately embody the design specification and logical design for proper operation of the device. Accordingly, after it has been created during a synthesis process, the physical design data is compared with the original logical design schematic in a process sometimes referred to as a "layout-versus-schematic" (LVS) process.

Once the correctness of the logical design has been verified, and geometric data corresponding to the logical design has been created in a layout design, the geometric data then may be analyzed. For example, because the physical design data is employed to create masks used at a foundry, the data must conform to the foundry's requirements. Each foundry specifies its own physical design parameters for compliance with their processes, equipment, and techniques. Accordingly, the design flow may include a process to confirm that the design data complies with the specified parameters. During this process, the physical layout of the circuit design is compared with design rules in a process commonly referred to as a "design rule check" (DRC) process. In addition to rules specified by the foundry, the design rule check process may also check the physical layout of the circuit design against other design rules, such as those obtained from test chips, general knowledge in the industry, previous manufacturing experience, etc.

With modern electronic design automation design flows, a designer may additionally employ one or more "design-for-manufacture" (DFM) software tools. As previously noted, design rule check processes attempt to identify, e.g., elements representing structures that will almost certainly be improperly formed during a manufacturing process. "Design-For-Manufacture" tools, however, provide processes that attempt to identify elements in a design representing structures with a significant likelihood of being improperly formed during the manufacturing process. A "design-for-manufacture" process may additionally determine what impact the improper formation of the identified elements will have on the yield of devices manufactured from the circuit design, and/or modifications that will reduce the likelihood that the identified elements will be improperly formed during the manufacturing process. For example, a "design-for-manufacture" (DFM) software tool may identify wires that are connected by only a single via, determine the yield impact for manufacturing a circuit from the design based upon the probability that each individual single via will be improperly formed during the manufacturing process, and then identify areas where redundant vias can be formed to supplement the single vias.

It should be noted that, in addition to "design-for-manufacture," various alternate terms are used in the electronic design automation industry. Accordingly, as used herein, the term "design-for-manufacture" or "design-for-manufacturing" is intended to encompass any electronic design automation process that identifies elements in a design representing structures that may be improperly formed during the manufacturing process. Thus, "design-for-manufacture" (DFM) software tools will include, for example, "lithographic friendly design" (LFD) tools that assist designers to make trade-off decisions on how to create a circuit design that is more robust and less sensitive to lithographic process windows. They will also include "design-for-yield" (DFY) electronic design automation tools, "yield assistance" electronic design automation tools, and "chip cleaning" and "design cleaning" electronic design automation tools.

After a designer has used one or more geometry analysis processes to verify that the physical layout of the circuit design is satisfactory, the designer may then perform one or more simulation processes to simulate the operation of a manufacturing process, in order to determine how the design will actually be realized by that particular manufacturing process. A simulation analysis process may additionally modify the design to address any problems identified by the simulation. For example, some design flows may employ one or more processes to simulate the image formed by the physical layout of the circuit design during a photolithographic process, and then modify the layout design to improve the resolution of the image that it will produce during a photolithography process.

These resolution enhancement techniques (RET) may include, for example, modifying the physical layout using optical proximity correction (OPC) or by the addition of sub-resolution assist features (SRAF). Other simulation analysis processes may include, for example, phase shift mask (PSM) simulation analysis processes, etch simulation analysis processes and planarization simulation analysis processes. Etch simulation analysis processes simulate the removal of materials during a chemical etching process, while planarization simulation processes simulate the polishing of the circuit's surface during a chemical-mechanical etching process. These simulation analysis processes may identify, for example, regions where an etch or polishing process will not leave a sufficiently planar surface. These simulation analysis processes may then modify the physical layout design to, e.g., include more geometric elements in those regions to increase their density.

Once a physical layout design has been finalized, the geometric elements in the design are formatted for use by a mask or reticle writing tool. Masks and reticles typically are made using tools that expose a blank reticle or mask substrate to an electron or laser beam (or to an array of electron beams or laser beams), but most mask writing tools are able to only "write" certain kinds of polygons, however, such as right triangles, rectangles or other trapezoids. Moreover, the sizes of the polygons are limited physically by the maximum beam (or beam array) size available to the tool. Accordingly, the larger geometric elements in a physical layout design data will typically be "fractured" into the smaller, more basic polygons that can be written by the mask or reticle writing tool.

It should be appreciated that various design flows may repeat one or more processes in any desired order. Thus, with some design flows, geometric analysis processes can be interleaved with simulation analysis processes and/or logical analysis processes. For example, once the physical layout of the circuit design has been modified using resolution enhancement techniques, then a design rule check process or design-for-manufacturing process may be performed on the modified layout, Further, these processes may be alternately repeated until a desired degree of resolution for the design is obtained. Similarly, a design rule check process and/or a design-for-manufacturing process may be employed after an optical proximity correction process, a phase shift mask simulation analysis process, an etch simulation analysis process or a planarization simulation analysis process. Examples of electronic design tools that employ one or more of the logical analysis processes, geometry analysis processes or simulation analysis processes discussed above are described in U.S. Pat. No. 6,240,299 to McSherry et al., issued May 8, 2001, U.S. Pat. No. 6,249,903 to McSherry et al., issued Jun. 19, 2001, U.S. Pat. No. 6,339,836 to Eisenhofer et al., issued Jan. 15, 2002, U.S. Pat. No. 6,397,372 to Bozkus et al., issued May 28, 2002, U.S. Pat. No. 6,415,421 to Anderson et al., issued Jul. 2, 2002, and U.S. Pat. No. 6,425,113 to Anderson et al., issued Jul. 23, 2002, each of which are incorporated entirely herein by reference.

Software Tools for Simulation, Verification or Modification of a Circuit Layout

To facilitate an understanding of various embodiments of the invention, one such software tool for automatic design automation, directed to the physical analysis and modification of a design for an integrated circuit, will now be generally described.

Figure 4:
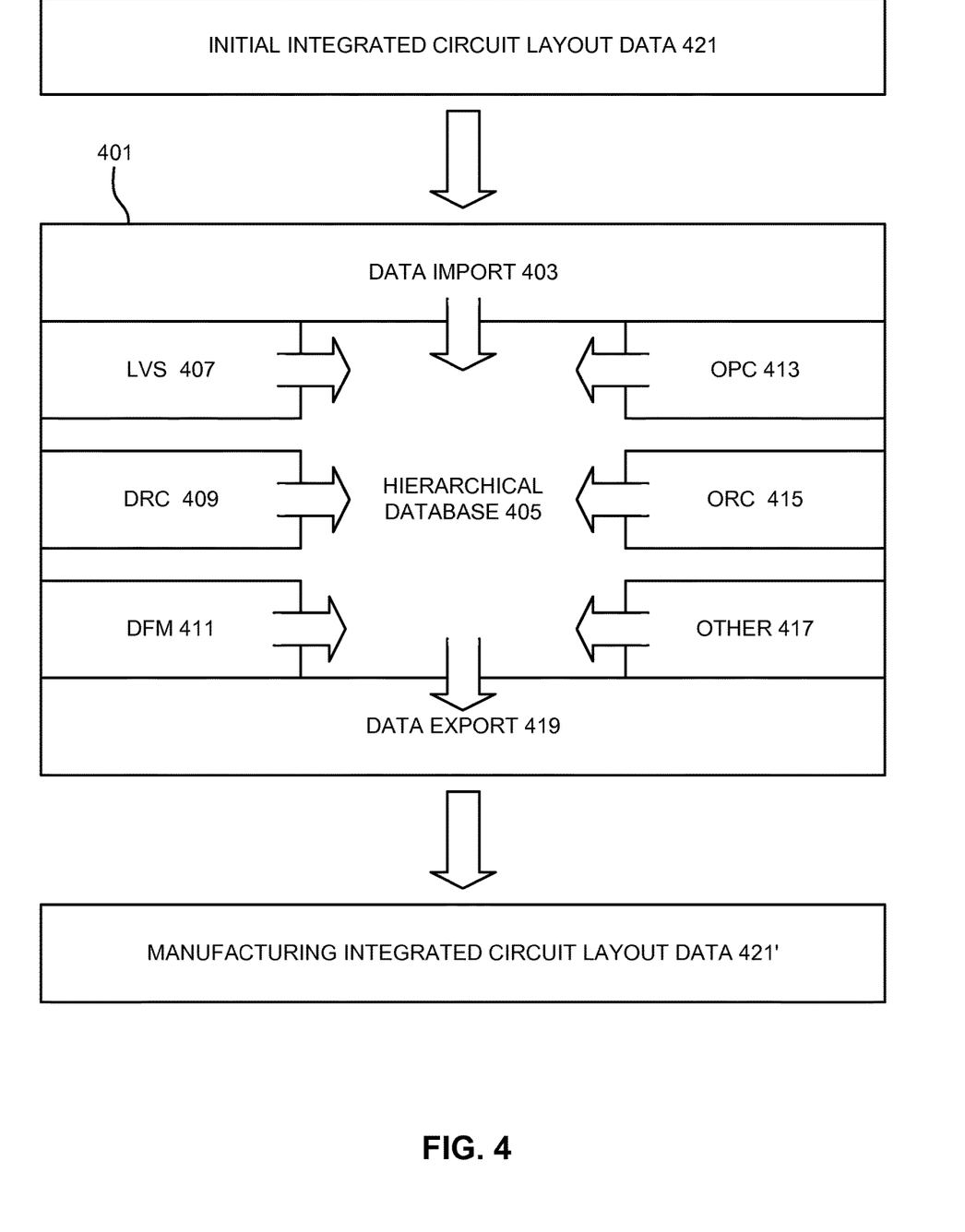
FIG. 4 schematically illustrates an example of a family of software tools for automatic design automation that may be used to perform a physical analysis of a circuit design according to various embodiments of the invention.

As seen in FIG. 3, an analysis tool 401, which may be implemented by a variety of different software applications, includes a data import module 403 and a hierarchical database 405. The analysis tool 401 also includes a layout-versus-schematic (LVS) verification module 407, a design rule check (DRC) module 409, a design-for-manufacturing (DFM) module 411, an optical proximity correction (OPC) module 413, and an optical proximity rule check (ORC) module 415. The analysis tool 401 may further include other modules 417 for performing additional functions as desired, such as a phase shift mask (PSM) module (not shown), an etch simulation analysis module (not shown) and/or a planarization simulation analysis module (not shown). The tool 401 also has a data export module 419. One example of such an analysis tool is the Calibre® family of software applications available from Mentor Graphics Corporation of Wilsonville, Oreg.

Initially, the tool 401 receives data 421 describing a physical layout design for an integrated circuit. The layout design data 421 may be in any desired format, such as, for example, the Graphic Data System II (GDSII) data format or the Open Artwork System Interchange Standard (OASIS) data format proposed by Semiconductor Equipment and Materials International (SEMI). Other formats for the data 421 may include an open source format named Open Access, Milkyway by Synopsys, Inc., and EDDM by Mentor Graphics, Inc. The layout data 421 includes geometric elements for manufacturing one or more portions of an integrated circuit device. For example, the initial integrated circuit layout data 421 may include a first set of polygons for creating a photolithographic mask that in turn will be used to form an isolation region of a transistor, a second set of polygons for creating a photolithographic mask that in turn will be used to form a contact electrode for the transistor, and a third set of polygons for creating a photolithographic mask that in turn will be used to form an interconnection line to the contact electrode. The initial integrated circuit layout data 421 may be converted by the data import module 403 into a format that can be more efficiently processed by the remaining components of the tool 401.

Once the data import module 403 has converted the original integrated circuit layout data 421 to the appropriate format, the layout data 421 is stored in the hierarchical database 405 for use by the various operations executed by the modules 405-417. Next, the layout-versus-schematic module 407 checks the layout design data 421 in a layout-versus-schematic process, to verify that it matches the original design specifications for the desired integrated circuit. If discrepancies between the layout design data 421 and the logical design for the integrated circuit are identified, then the layout design data 421 may be revised to address one or more of these discrepancies. Thus, the layout-versus-schematic process performed by the layout-versus-schematic module 407 may lead to a new version of the layout design data with revisions. According to various implementations of the invention tool 401, the layout data 421 may be manually revised by a user, automatically revised by the layout-versus-schematic module 407, or some combination thereof.

Next, the design rule check module 409 confirms that the verified layout data 421 complies with defined geometric design rules. If portions of the layout data 421 do not adhere to or otherwise violate the design rules, then the layout data 421 may be modified to ensure that one or more of these portions complies with the design rules. The design rule check process performed by the design rule check module 409 thus also may lead to a new version of the layout design data with various revisions. Again, with various implementations of the invention tool 401, the layout data 421 may be manually modified by a user, automatically modified by the design rule check module 409, or some combination thereof.

The modified layout data 421 is then processed by the design for manufacturing module 411. As previously noted, a "design-for-manufacture" processes attempts to identify elements in a design representing structures with a significant likelihood of being improperly formed during the manufacturing process. A "design-for-manufacture" process may additionally determine what impact the improper formation of the identified structures will have on the yield of devices manufactured from the circuit design, and/or modifications that will reduce the likelihood that the identified structures may be improperly formed during the manufacturing process. For example, a "design-for-manufacture" (DFM) software tool may identify wires that are connected by single vias, determine the yield impact based upon the probability that each individual single via will be improperly formed during the manufacturing process, and then identify areas where redundant visa can be formed to supplement the single vias.

The processed layout data 421 is then passed to the optical proximity correction module 413, which corrects the layout data 421 for manufacturing distortions that would otherwise occur during the lithographic patterning. For example, the optical proximity correction module 413 may correct for image distortions, optical proximity effects, photoresist kinetic effects, and etch loading distortions. The layout data 421 modified by the optical proximity correction module 413 then is provided to the optical process rule check module 415

The optical process rule check module 415 (more commonly called the optical rules check module or ORC module) ensures that the changes made by the optical proximity correction module 413 are actually manufacturable, a "downstream-looking" step for layout verification. This compliments the "upstream-looking" step of the LVS performed by the LVS module 407 and the self-consistency check of the DRC process performed by the DRC module 409, adding symmetry to the verification step. Thus, each of the processes performed by the design for manufacturing process 411, the optical proximity correction module 413, and the optical process rule check module 415 may lead to a new version of the layout design data with various revisions.

As previously noted, other modules 417 may be employed to perform alternate or additional manipulations of the layout data 421, as desired. For example, some implementations of the tool 401 may employ, for example, a phase shift mask module. As previously discussed, with a phase-shift mask (PSM) analysis (another approach to resolution enhancement technology (RET)), the geometric elements in a layout design are modified so that the pattern they create on the reticle will introduce contrast-enhancing interference fringes in the image. The tool 401 also may alternately or additionally employ, for example, an etch simulation analysis processes or a planarization simulation analysis processes. The process or processes performed by each of these additional modules 417 may also lead to the creation of a new version of the layout data 421 that includes revisions. The tool 401 also may alternately or additionally employ, for example, a layout parasitic extraction module After all of the desired operations have been performed on the initial layout data 421, the data export module 419 converts the processed layout data 421 into manufacturing integrated circuit layout data 423 that can be used to form one or more masks or reticules to manufacture the integrated circuit (that is, the data export module 419 converts the processed layout data 421 into a format that can be used in a photolithographic manufacturing process). Masks and reticles typically are made using tools that expose a blank reticle or mask substrate to an electron or laser beam (or to an array of electron beams or laser beams), but most mask writing tools are able to only "write" certain kinds of polygons, however, such as right triangles, rectangles or other trapezoids. Moreover, the sizes of the polygons are limited physically by the maximum beam (or beam array) size available to the tool.

Accordingly, the data export module 419 may "fracture" larger geometric elements in the layout design, or geometric elements that are not right triangles, rectangles or trapezoids (which typically are a majority of the geometric elements in a layout design) into the smaller, more basic polygons that can be written by the mask or reticle writing tool. Of course, the data export module 419 may alternately or additionally convert the processed layout data 421 into any desired type of data, such as data for use in a synthesis process (e.g., for creating an entry for a circuit library), data for use in a place-and-route process, data for use in calculating parasitic effects, etc. Further, the tool 401 may store one or more versions of the layout 421 containing different modifications, so that a designer can undo undesirable modifications. For example, the hierarchical database 405 may store alternate versions of the layout data 421 created during any step of the process flow between the modules 407-417.

Logic-Driven Layout Verification

Figure 5:
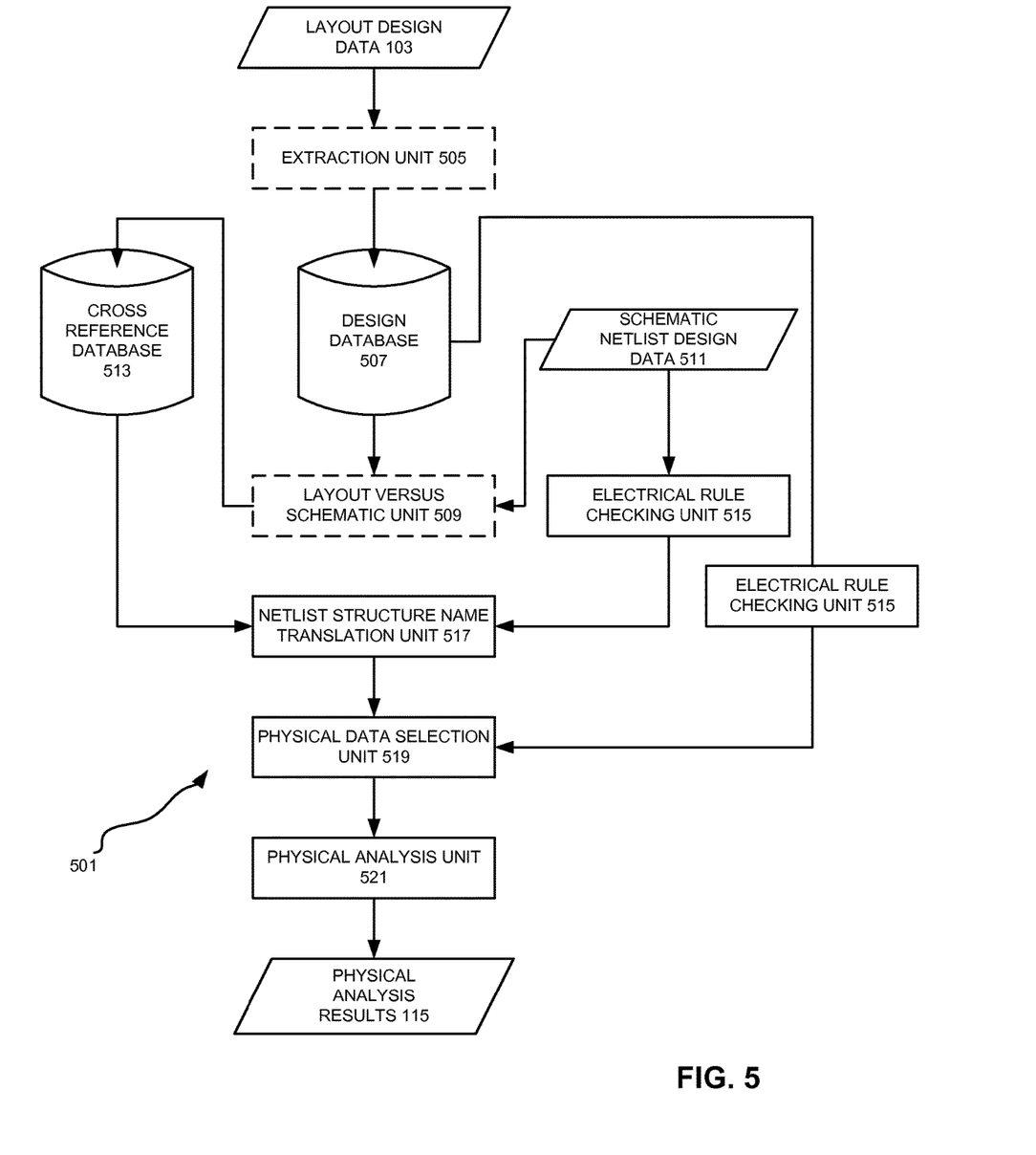
FIG. 5 illustrates a tool for performing a physical analysis of a circuit design based upon logical information that may be employed according to various embodiments of the invention.

FIG. 5 illustrates an example of a logic-driven layout verification tool 501 that may be implemented according to various examples of the invention. As will be appreciated by those of ordinary skill in the art, the various units making up the logic-driven layout verification tool 501 may be implemented using computer-executable software instructions executed by one or more programmable computing devices, by computer-executable software instructions tangibly and non-transitorily stored on a computer readable medium (such as a magnetic or optical memory storage device) for execution by one or more programmable computing devices, or some combination thereof.

As seen in this figure, the logic-driven layout verification tool 501 optionally includes an extraction unit 505 and a layout-versus-schematic unit 509. Further, the logic-driven layout verification tool 501 includes an electrical rule checking unit 515, and netlist structure name translation unit 517, a physical data selection unit 519, and a physical analysis unit 521. One possible operation of the logic-driven layout verification tool 501 will be describe with regard to the process illustrated in the flowchart shown in FIG. 6.

Figure 6A:
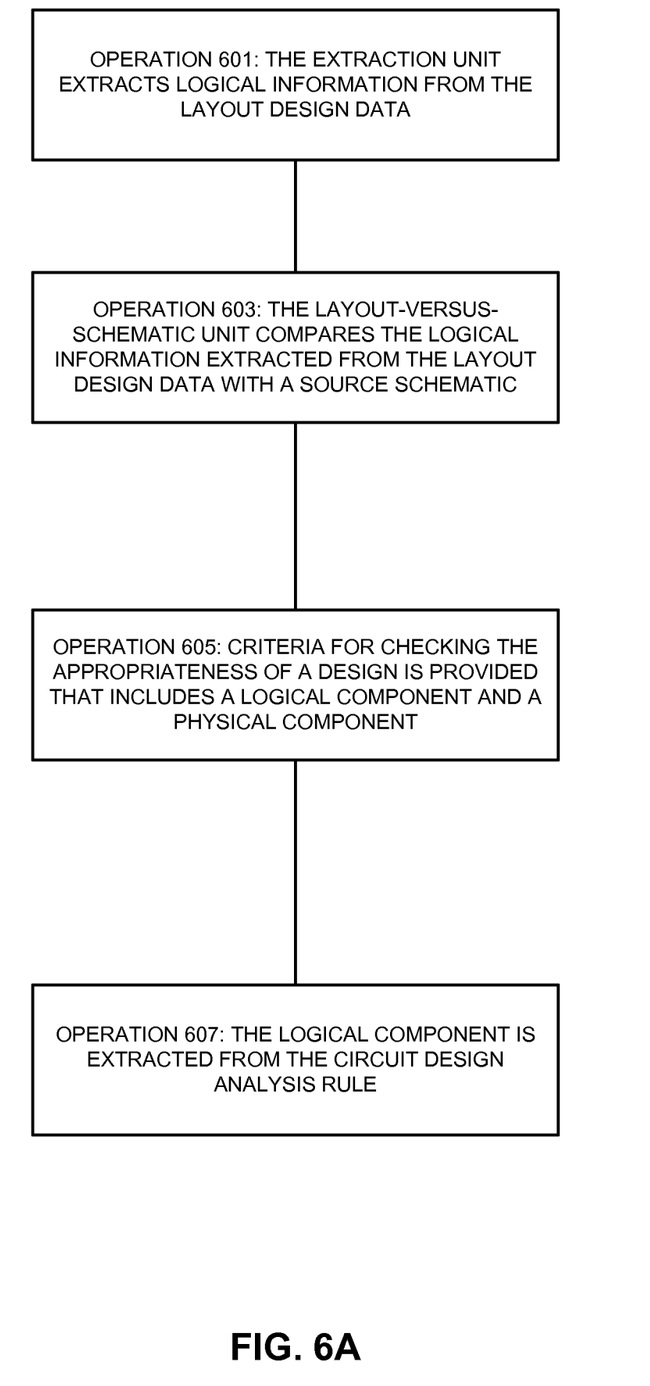
FIG. 6 illustrates a method of performing a physical analysis of a circuit design based upon logical information that may be employed by various embodiments of the invention.
Figure 6B:
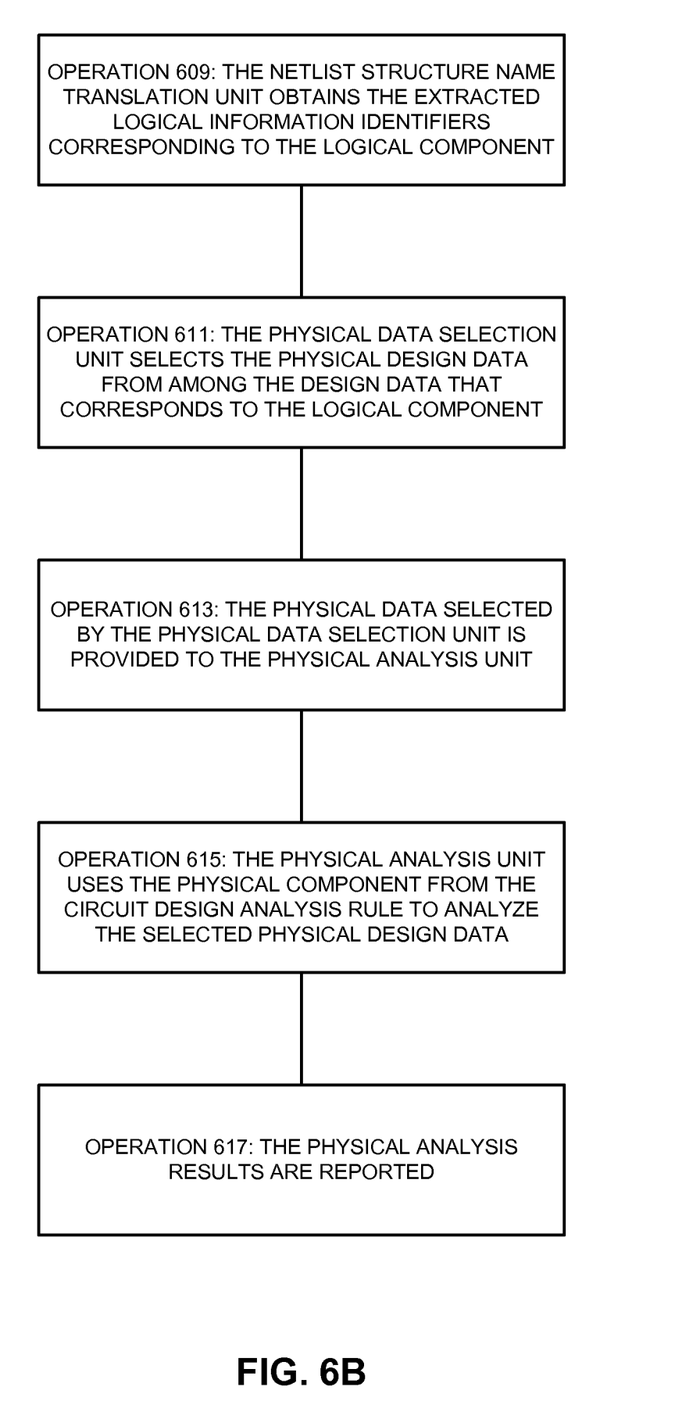

Initially, in operation 601, the extraction unit 505 extracts logical information from the layout design data 103. The extraction of logical information is a well-known process to those of ordinary skill in the art, and thus will not be discussed in more detail. The layout design data 103, along with the extracted logical information, may be stored in a design database 507.

Next, in operation 603, the layout-versus-schematic unit 509 compares the logical information extracted from the layout design data 103 with schematic netlist design data 511. As will be appreciated, the schematic netlist design data 511 may be the source schematic logical circuit design used to produce the layout design data 103. As such, the schematic netlist design data 511 may employ arbitrary logical object names that do not have names corresponding to any logical objects extracted from the layout design data 103 by the extraction unit 505. Accordingly, the layout-versus-schematic unit 509 may create a cross-reference database 513, cross referencing logical names (or other identifiers) employed in the source schematic netlist design data 511 with the logical information extracted from the layout design data 103 by the extraction unit 505.

With some embodiments of the invention, the extraction unit 505, the layout-versus-schematic unit 509, or both may be implemented using the Calibre family of tools available from Mentor Graphics Corporation of Wilsonville, Oreg. Further, while some implementations may include the extraction unit 505, the layout-versus-schematic unit 509, or both, it should be appreciated that various implementations of the invention may omit one or both of these units. That is, with some implementations of the invention, the cross-referencing information may have already been generated. Still further, some implementations may operate entirely with logical information previously extracted from the layout design data 103, omitting the need for cross-referencing information (and the netlist structure name translation unit 517, described below).

Next, in operation 605, a user (for example, an integrated circuit designer or manufacturer) provides criteria for checking the appropriateness of a design. Typically, these checking criteria will be in the form of a circuit design analysis rule 105, as previously noted. As seen in FIG. 1, above, the circuit design analysis rule 105 includes a logical component 107 and a physical component 109. The logical component 107 will specify some type of structure or other object in a logical circuit design, such as a netlist. Typically, the logical component 107 will be a circuit device (for example, MOS field-effect transistors) or an arrangement of circuit devices into a particular configuration (for example, a 1-bit SRAM circuit), but various implementations of the invention may allow the logical component 107 to specific any desired logical design object.

The physical component 109 similarly may be any criteria that can be applied to analyze physical design data. Typically, the physical component 109 will be some type of physical measurement criteria, such as a minimum width determination, a maximum distance determination, an area ratio determination, and the like. Of course, the physical component 109 may include any desired criteria desired for analyzing physical circuit design data.

Next, in operation 607, the logical component 107 is extracted from the schematic netlist design data 511 using the circuit design analysis rule 105 by the electrical rule checking unit 515. With various examples of the invention, the electrical rule checking unit 515 may be implemented using, for example, the Programmable Electrical Rule Checking tool provided in the Calibre® family of tools available from Mentor Graphics Corporation of Wilsonville, Oreg.

When the logical component 107 employs logical object names from the schematic netlist design data 511, then, in operation 609, the netlist structure name translation unit 517 obtains the extracted logical information identifiers corresponding to the logical component 107 from the cross-reference database 513. Next, in operation 611, the physical data selection unit 519 then selects the physical design data from among the design data 103 that corresponds to the logical component 107. With some embodiments of the invention, the physical data selection unit 519 may be implemented using the YieldServer tool provided in the Calibre® family of tools available from Mentor Graphics Corporation of Wilsonville, Oreg.

It should be appreciated that some implementations of the invention may be employed without schematic netlist design data 511, instead using only the logical netlist data extracted from the layout design data 103. The logical component 107 is then extracted from the logical netlist data using the circuit design analysis rule 105 by the electrical rule checking unit 515.

With these implementations, the physical data selection unit 519 may be implemented as an application programming interface (API) for the electrical rule checking unit 515, to select the physical data in the design database 507 corresponding to the logical name (or other identification information) obtained by the electrical rule checking unit 515 from logical component. With still other implementations, however, the electrical rule checking unit 515 may incorporate the functionality of the physical data selection unit 519, and select the relevant physical data directly from in the design database 507. This implementation may be employed, e.g., to obviate the need to use netlist information, and to instead select the raw physical data directly from within the design database 507.

Next, in operation 613, the physical data selected by the physical data selection unit 519 is provided to the physical analysis unit 521. The physical analysis unit 521 then uses the physical component 109 from the circuit design analysis rule 105 to analyze the selected physical design data in operation 615, thereby producing physical analysis results 115. In operation 617, the physical analysis results 115 are reported to a user. With various implementations of the invention, the physical analysis results 115 may be processed by the netlist structure name translation unit 517 to provide cross-referencing information.

While the design database 507 and the cross reference database 513 are shown as separate units in FIG. 5, a single computer accessible medium may be used to implement the two databases as a central database. Further, one or more of the layout design data 103, the schematic netlist design data 511, and the physical analysis results 115 may be stored in the central database.

The above two cases are just examples of a rule file for illustration purposes. They are not exhaustive and should not be used to limit the scope of the invention. Moreover, the logic of interest and the corresponding layout requirements may be stored in the same physical medium or in different physical media. They may be saved in the same logical file or different logical files.

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims. For example, while specific terminology has been employed above to refer to electronic design automation processes, it should be appreciated that various examples of the invention may be implemented using any desired combination of electronic design automation processes.

Thus, in addition to use with "design-for-manufacture" processes, various examples of the invention can be employed with "design-for-yield" (DFY) electronic design automation processes, "yield assistance" electronic design automation processes, "lithographic-friendly-design" (LFD) electronic design automation processes, including "chip cleaning" and "design cleaning" electronic design automation processes, etc. Likewise, in addition to use with "design-rule-check" electronic design automation processes, various implementations of the invention may be employed with "physical verification" electronic design automation processes. Also, in addition to being used with OPC and ORC electronic design automation processes, various implementations of the invention may be used with any type of resolution enhancement electronic design automation processes.

What is claimed is:
1. A method comprising:
  accessing a circuit design analysis rule that comprises:
    a logical component that specifies a specific logical design object; and
    a physical component specifying physical analysis criteria to be applied to the specific logical design object;
  identifying instances of the specific logical design object in a logical circuit design;
  identifying physical structures in layout design data that correspond to the instances of the specific logical design object identified in the logical circuit design;
  applying the physical analysis criteria to the physical structures that correspond to each instance of the specific logical design object, wherein the logical circuit design is a source schematic logical circuit design; and
further comprising:
  extracting logical design data from the layout design data to obtain an extracted logical circuit design;

correlating logical names in the source schematic logical circuit design to extracted logical design data identifiers that identify portions of the extracted logical circuit design; and tracking correlations between the logical names in the source schematic logical circuit design to the extracted logical design data identifiers in a cross-reference database.

2. The method of claim 1, wherein the logical circuit design comprises netlist data; and wherein identifying instances of the specific logical design object in the logical circuit design comprises:
traversing the netlist data;
identifying elements in the netlist data that correspond to the specific logical design object; and
exporting the identified elements as collections of pin-pairs, nets, devices, or instances.

3. The method of claim 2, wherein each collection corresponds to a particular instance of the specific logical design object.

4. The method of claim 2, wherein identifying the physical structures in the layout design data that correspond to the instances of the specific logical design object comprises:
identifying portions of the layout design data corresponding to the identified elements of the netlist data.

5. The method of claim 2, further comprising extracting the netlist data from the layout design data.

6. The method of claim 1, wherein identifying the physical structures in the layout design data comprises:
obtaining, from the cross-reference database, particular extracted logical design data identifiers for the portions of the extracted logical circuit design that correspond to the instances of the specific logical design object identified in the source schematic logical circuit design; and
identifying the physical structures from the layout design data that correspond to the particular extracted logical design data identifiers.

7. The method of claim 1, wherein the physical analysis criteria comprises a design rule check or a design-for-manufacturing check.

8. A non-transitory machine-readable medium comprising instructions that, when executed by a processor, cause a system to:
access a circuit design analysis rule that comprises:
a logical component that specifies a specific logical design object; and
a physical component specifying physical analysis criteria to be applied to the specific logical design object;
identify instances of the specific logical design object in a logical circuit design;
identify physical structures in layout design data that correspond to the instances of the specific logical design object identified in the logical circuit design; and
apply the physical analysis criteria to the physical structures that correspond to each instance of the specific logical design object, wherein the logical circuit design is a source schematic logical circuit design; and
further comprising instructions that, when executed by the processor, cause the system to:
extract logical design data from the layout design data to obtain an extracted logical circuit design;
correlate logical names in the source schematic logical circuit design to extracted logical design data identifiers that identify portions of the extracted logical circuit design; and track correlations between the logical names in the source schematic logical circuit design to the extracted logical design data identifiers in a cross-reference database.

9. The non-transitory machine-readable medium of claim 8, wherein the logical circuit design comprises netlist data; and wherein the instructions to identify instances of the specific logical design object in the logical circuit design comprises instructions that cause the system to:
traverse the netlist data;
identify elements in the netlist data that correspond to the specific logical design object; and
export the identified elements as collections of pin-pairs, nets, devices, or instances.

10. The non-transitory machine-readable medium of claim 9, wherein each collection corresponds to a particular instance of the specific logical design object.

11. The non-transitory machine-readable medium of claim 9, wherein the instructions to identify the physical structures in the layout design data that correspond to the instances of the specific logical design object comprise instructions that cause the system to:
identify portions of the layout design data corresponding to the identified elements of the netlist data.

12. The non-transitory machine-readable medium of claim 9, further comprising instructions that cause the system to extract the netlist data from the layout design data.

13. The non-transitory machine-readable medium of claim 8, wherein the instructions to identify the physical structures in the layout design data comprise instructions that cause the system to:
obtain, from the cross-reference database, particular extracted logical design data identifiers for the portions of the extracted logical circuit design that correspond to the instances of the specific logical design object identified in the source schematic logical circuit design; and
identify the physical structures from the layout design data that correspond to the particular extracted logical design data identifiers.

14. A system comprising:
a processor; and
a non-transitory machine-readable medium storing instructions that, when executed by the processor, cause the processor to:
access layout design data of a circuit;
extract logical design data from the layout design data;
cross reference the extracted logical design data with logical object names of a schematic netlist and store the cross references in a cross-reference database;
access a circuit design analysis rule that comprises:
a logical component that specifies a specific logical design object using a logical object name from the schematic netlist; and
a physical component specifying physical analysis criteria to be applied to the specific logical design object;
identify instances of the specific logical design object in the schematic netlist;
identify physical structures in the layout design data that correspond to the instances of the specific logical design object identified in schematic netlist using the cross-reference database; and
apply the physical analysis criteria to the physical structures that correspond to each instance of the specific logical design object.

* * * * *